United States Patent
Hur

(10) Patent No.: US 6,204,592 B1
(45) Date of Patent: Mar. 20, 2001

(54) ULTRASONIC NAILING AND DRILLING APPARATUS

(76) Inventor: Ben Hur, 533 E. Lemon Ave., Arcadia, CA (US) 91006

( * ) Notice: Subject to any disclaimer, the term of this patent is extended or adjusted under 35 U.S.C. 154(b) by 0 days.

(21) Appl. No.: 09/416,239

(22) Filed: Oct. 12, 1999

(51) Int. Cl.⁷ ........................................... H02N 2/00
(52) U.S. Cl. ............................. 310/323.18; 310/323.12; 310/323.19; 310/346
(58) Field of Search ..................... 310/323.12, 323.18, 310/323.19, 325, 341, 346; 451/124, 165

(56) References Cited

U.S. PATENT DOCUMENTS

| | | | |
|---|---|---|---|
| 3,619,671 | * 11/1971 | Shoh | 310/323.12 |
| 4,169,984 | 10/1979 | Parisi | 310/323 |
| 4,319,716 | * 3/1982 | Lauer | 239/102 |
| 4,828,052 | 5/1989 | Duran | 175/55 |
| 4,838,853 | 6/1989 | Parisi | 604/22 |
| 4,869,715 | 9/1989 | Sherburne | 604/22 |
| 5,144,771 | * 9/1992 | Miwa | 51/59 SS |
| 5,904,615 | * 5/1999 | Jeong et al. | 451/443 |

* cited by examiner

*Primary Examiner*—Thomas M. Dougherty
(74) *Attorney, Agent, or Firm*—John K. Park; Park & Sutton

(57) ABSTRACT

A highly efficient and effective ultrasonic nailing and drilling apparatus for various precision use, such as medical or dental surgery, comprises of a piezoelectric transducer means to give an axial thrust and a motor to give a rotation to a bit. Therefore, this ultrasonic nailing and drilling apparatus combines the best of the ultrasound nailing or drilling bit and the best of the rotational drill. The ultrasonic nailing and drilling apparatus further comprises of an elongated horn having an operative tip, wherein a bit can be fixedly attached. The operative tip can be in any form designed to for ultrasonic machines, and even can be in a similar shape as a flat screwdriver tip, as a Phillips head tip, or even as a conventional drill bit.

12 Claims, 4 Drawing Sheets

15

15

15   22

ULTRASONIC NAILING AND DRILLING APPARATUS

BACKGROUND OF THE INVENTION

This present invention relates to a ultrasonic nailing and drilling apparatus for nailing and drilling. More particularly, this present invention relates to toward a highly efficient and effective ultrasonic nailing and drilling for various precision use, such as medical or dental surgery. However, although the present invention is specially adapted as a medical device, but its application is not limited to the medical field.

Surgical procedures involving the use of an ultrasonic probe for removing tissue are well known. Various ultrasonic probes having operative tips that are caused to vibrate at frequencies between about 30,000 Hz and 60,000 Hz with a stroke of about 20 μm to 150 μm are applied depending on its usage for industrial or medical purpose.

For conventional drilling method, material and drill bits are stuck with each other thereby resulting in more friction. In addition, their effectiveness and efficiency has yet to be improved. That is, it is necessary for a drilling machine to generate a lower speed at high torques but torque versus speed characteristics in known electrical motors do not meet the requirements for such precision works.

When a drilling bit is turned (resonated) by ultrasonic wave and rotated by a power train such as motor, it will be more effective. The drill bit is almost floated from material (not stuck with each other) because of its rotational speed and longitudinal amplitude (stroke) both of which can be adjusted to each other so as to create the best efficiency. Moreover, certain drilling bits can be nails. When it is fully plugged into a material, it also can be removed by a machine tool due to reversed rotation. In addition, it can be used as anchor preparation. It can drill a small hole where anchor can be nailed tightly into a bone or other material.

Similarly, in ultrasonic drilling, although the drilling was useful to drill into hard materials, such as boron carbide, glass, titanium carbide, steel, bone, and the like, the drill itself was limited to chipping away the surface with a tubular drill bit. However, it has been very impractical to drill a deep hole, even with the diamond tipped drill bit, as the material became harder and as the chipped away materials were trapped within the hollow bit.

Therefore, it is an object of this invention to provide a ultrasonic nailing and drilling apparatus that not only impart vertical impact on the material, but also a rotational force simultaneously upon the material through the bit.

Also, it is another object of the invention to rapidly drill holes or nail into hard surfaces without undue mechanical or thermal stress to the bit or the material. Moreover, it is an object of this invention to be able to use various nails and drilling bits, including drilling bits similar to conventional drill bits.

It is also another object of the invention to make the use of the present invention simple and the device small enough to be held in a single hand of the user. Moreover, it is also desired that bits can be easily changed without much downtime or difficulties.

Additional objects, advantages, and novel features of the present invention will be set forth in part in the description that follow, and in part will be apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing objects and other objects, and accordance of the purpose of this invention, as embodied and broadly described herein, a highly efficient and effective ultrasonic nailing and drilling apparatus for various precision use, such as medical (bone) surgery, comprises of a piezoelectric transducer means to give an axial thrust and a motor to give a rotation to a bit.

The ultrasonic nailing and drilling apparatus further comprises an elongated horn. Either exponential horn or stepped horn can be used depending on purpose. The exponential horn has low Q (quality factor) and wider resonating frequency range. The stepped horn has high Q and high gain (amplitude) which can be measured by surface ratio of a front area of horn, a rear area of horn and a shape of horn.

The piezoelectric transducer means is a source of a mechanical longitudinal stroke to the elongated horn which amplifies and transmits the amplified mechanical axial stroke to the operative tip. Here, the length of the elongated horn is determined by $[\lambda(2n+1)]/4$ ($\lambda$=wave length, n=0, 1, 2 . . . ) from a nodal point to maximize the amplitude to its highest stroke.

This ultrasonic nailing and drilling apparatus combines the best of the ultrasound nailing or drilling bit and the best of the rotational drill. Moreover, although the present invention is specially adapted as a medical device, but its application is not limited to the medical field.

The ultrasonic nailing and drilling apparatus further comprises of an elongated horn. The elongated horn has two ends, a first horn end and a second horn end. The first horn end forms an operative tip, wherein a bit can be fixedly attached. The operative tip can be in any form designed to for ultrasonic machines, and even can be in a similar shape as a flat screwdriver tip, as a Phillips head tip, or even as a conventional drill bit. However, the bits should be made of a high strength material such as a stainless steel and a titanium alloy.

The ultrasonic nailing and drilling apparatus further comprises of a shroud that houses the piezoelectric transducer means. The piezoelectric means is generally a ceramic piezoelectric transducer, but other piezoelectric transducer can be used. The piezoelectric transducer means should have an axial bore, and wherein the second horn end of the elongated horn extends through the axial bore of the piezoelectric transducer means. The second horn end of the elongated horn extending through the axial bore helps to transmit the vibration of the piezoelectric transducer means to the elongated horn; thus to the operative tip.

The ultrasonic nailing and drilling apparatus further comprises of a housing, wherein the shroud is rotatably attached within the housing. The piezoelectric transducer means and the elongated horn are fixedly attached within the shroud, but the elongated horn and the operative tip extend out of the shroud. The shroud should be able to freely rotate within housing. For the best performance, the housing should be a self lubricating bearing so the shroud can rotate nearly frictionless within the housing.

For better performance of the ultrasonic nailing and drilling apparatus, housing can comprises of a horn cover and a house bearing. The horn cover has a first cover end and a second cover end, wherein the horn cover encloses a substantial portion of the elongated horn. The first cover end is located toward the operative tip, and the second cover end is fixedly attached to the house bearing. In this configuration, the house bearing is the portion of the housing that rotatably houses the shroud.

The motor has a rotating arm. The motor is fixedly attached to the housing, but the rotating arm is fixedly attached to the shroud so that the shroud rotates as the rotating arm rotates. Therefore, when the ultrasonic nailing and drilling apparatus is switched on, the piezoelectric transducer means is activated to give axial impulses on the elongated horn, and the rotating arm of the motor rotates the shroud (and the piezoelectric transducer means within the shroud) to give rotation to the elongated horn. Therefore, the piezoelectric transducer means exerts axial impulses on the operative tip and the rotating arm of the motor exerts a rotation on the operative tip simultaneously.

For a best performance the motor should be a ultrasonic motor that is able to rotate the rotating arm bi-directionally; both clockwise and counter-clockwise, according to the need of the user. As the rotating arm rotates bi-directionally, the ultrasonic nailing and drilling apparatus can be used to screw in a screw into a very hard surface, and then to remove the screw out of a very hard surface. Moreover, the bit can be drilled into the hard surface and the bit can also be reversed out of the hard surface. The ultrasonic motor is ideal for a delicate and precise operation, such as for medical or dental operations, as the ultrasonic motor has high torque at lower rpm (revolutions per minute).

The ultrasonic nailing and drilling apparatus according to this invention is highly efficient and effective, especially when the elongated horn is fixedly attached to the shroud and rotatably attached to the horn cover at about two nodal points of the elongated horn. The first nodal point of the elongated horn is located towards the piezoelectric transducer means, and the second nodal point of the elongated horn is located towards the operative tip. The first nodal point of the elongated horn can easily reach the inner wall of the shroud if the elongated horn has a broad portion about the first nodal point of the elongated horn. The second nodal point of the elongated horn can be rotatably attached to the horn cover. The preferred version should have a cover bearing fixedly attached to the horn cover, yet the second nodal point of the elongated horn is rotatably attached to the cover bearing. It is preferred to have both the house bearing and the cover bearing are self lubricating bearings.

The nodal points of the ultrasonic wave created by the piezoelectric means are used to attached the elongated horn and the shroud, because when the nodal points are used, the vibration transmitted to the housing is very minimal and the loss of the ultrasonic energy created by the piezoelectric transducer means is minimized. Also, in order to minimize the loss of the ultrasonic energy, the point of contact at each of the nodal point should be also minimized. In order to achieve the minimization of the contact surface, rubber O-rings can be used near the contact points. Although the rubber O-rings do increase the overall surface area of the contact point, when the O-rings are made of rubber, the energy loss is minimized.

Because the shroud, along with the piezoelectric transducer means, need to be rotating, a preferred version of the ultrasonic nailing and drilling apparatus further comprises of a slip ring assembly attached to the housing or the shroud. The slip ring assembly comprises of a first ring and a second ring, wherein electrical power is supplied to the piezoelectric transducer means thorough the first ring and the second ring. The power to the slip ring assembly is supplied through the housing, and the power to the piezoelectric transducer is supplied through a brush or a cantilevered electrode brushing over the first ring and the second ring.

The most preferred version further comprises of the housing having a fluid inlet and a fluid outlet, wherein a cooling fluid can be forced into the fluid inlet and out of the fluid outlet to cool the ultrasonic nailing and drilling apparatus. Because the elongated horn can become very hot, cool air or even cold water can pass through the housing, through the horn cover. However, because a large amount of water over the elongate horn reduces the effectiveness of the ultrasonic effect of the piezoelectric transducer means transmitted through the elongated horn, cool or cold air is preferred.

To aid the torque from the rotating arm of the motor efficiently transfer to the shroud, and to provide more secure hold of the elongated horn and the piezoelectric transducer means within the housing, the preferred version should have a rear plate of the shroud so that the rotating arm of the motor is securely fixed to the rear plate of the shroud. The benefit of having the rear plate is that more stability to the shroud and the elongated horn can be achieved.

The operative tip of the elongated horn extends out of the housing. At the end of the operating tip is a means to capture a bit. There can be many conventional ways to capture the bit, including and not limited to a male and female threads, a clamping jaws (such as often used in regular power drill), and an outer sleeve that covers the end of the bit after the bit is securely attached to the operative tip.

The preferred version is the operative tip having a female thread that accepts the male threads of the bit, and the operative tip further having an outer sleeve that is also threaded, so that the outer surface of the bit can also be securely clamped. The outer sleeve of the operative tip should have a female thread that securely locks onto the male threads of the outer surface of the bit. This preferred version allows the drill to be able to drill into the material, and then retract the bit (or a screw) upon the reversing of the motor.

The benefits of this inventions are numerous. First, the bit can be drilled into the material and retracted out of the material. Second, the drilling using a ultrasonic device does not have to merely depend on the chipping action of the drill bit, but now actual rotation of the bit is possible. Third, the speed of the rotation can be easily adjusted according to the material being nailed into or drilled into. Fourth, even for a simple nailing procedure, the slow rotation of the nail tip can enhance the penetrating effect of the nail. Fifth, because of the ultrasonic effect from the piezoelectric transducer, the torque on the rotating arm does not need to be great. In fact, very little torque from the rotating arm can improve the drilling procedure as the rotating bit is also affecting the drilling surface ultrasonically.

Although the present invention is briefly summarized, the fuller understanding of the invention can be obtained by the following drawings, the detailed description and appended claims.

BRIEF DESCRIPTION OF THE DRAWINGS

The present invention will be better understood with reference to the accompanying drawings, wherein.

DETAILED DESCRIPTION OF THE PREFERRED EMBODIMENTS

With reference to the accompanying drawings, the ultrasonic nailing and drilling apparatus 10 according to the present invention will now be described.

Figure 1:
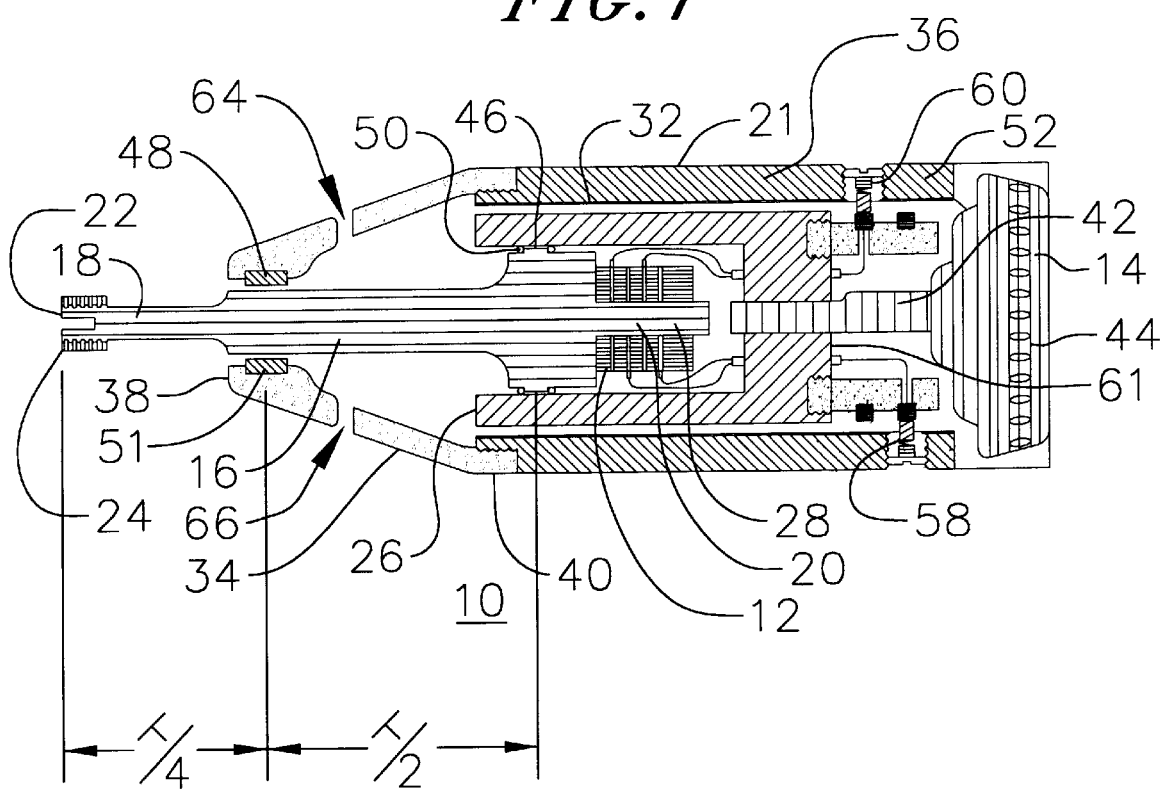
FIG. 1 is a cross-sectional view illustrating a ultrasonic nailing and drilling apparatus according to this invention.

As shown in FIG. 1, the ultrasonic nailing and drilling apparatus 10 comprises of a piezoelectric transducer means 12 to give an axial thrust and a motor 14 to give a rotation, respectively to a bit 15 (shown in FIGS. 3A–3B, 4A–4B and 5A–5C). A common form of the piezoelectric transducer means 12 can be a BLT (Boltclamped Langevin Type Transducer) composed of PZT (Piezoelectric Lead Zirconate Titanate Crystals).

The ultrasonic nailing and drilling apparatus 10 further comprises of an elongated horn 16, wherein either exponential horn or stepped horn can be used for the elongated horn 16 depending on purpose. Here, the exponential horn has low Q (quality factor) and wider resonating frequency range, and the stepped horn has high Q and high gain (amplitude) which can be measured by surface ratio of a front area of horn, a rear area of horn and a shape of horn. The elongated horn 16 may be formed of a high strength material such as a titanium alloy or an aluminum alloy.

The elongated horn 16 has two ends, a first horn end 18 and a second horn end 20. The piezoelectric transducer means 12, the motor 14, the elongated horn 16 are all housed by a housing 21. The first horn end 18 forms an operative tip 22, wherein a bit 15 can be fixedly attached.

The piezoelectric transducer means 12 is a source of a mechanical axial stroke to the elongated horn 16 which amplifies and transmits the amplified mechanical axial stroke to the operative tip 22. Here, the length of the elongated horn 16 is determined by $[\lambda(2n+1)]/4$ ($\lambda$=wave length, n=0, 1, 2 . . . ) to maximize the amplitude to its highest stroke.

The operative tip 22 can be in any form designed for ultrasonic machines, including a simple adapter for a bit 15. Moreover, the operative tip 22 can also be designed as a bit itself, including familiar shapes as a flat screwdriver tip, as a Phillips head tip, or even as a conventional drill bit. Whether the operative tip 22 accepts another bit 15, or the operative tip 22 itself is the bit, the bit 15 should be made of a high strength material such as a stainless steel or a titanium alloy.

The operative tip 22 of the elongated horn 16 extends out of the housing 21. At the end of the operative tip 22 is a means to capture a bit 15. There can be many conventional ways to capture the bit 15, including and not limited to a male and female threads, a clamping jaws (such as often used in regular power drill), and an outer sleeve that covers the end of the bit 15 after the bit 15 is securely attached to the operative tip 22.

Figure 5A:
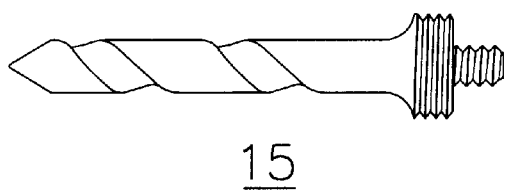
FIGS. 5A, 5b and 5C show various bits that can be used in this invention.
Figure 5B:
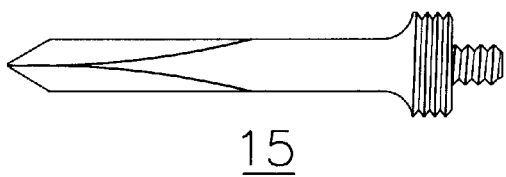
Figure 5C:
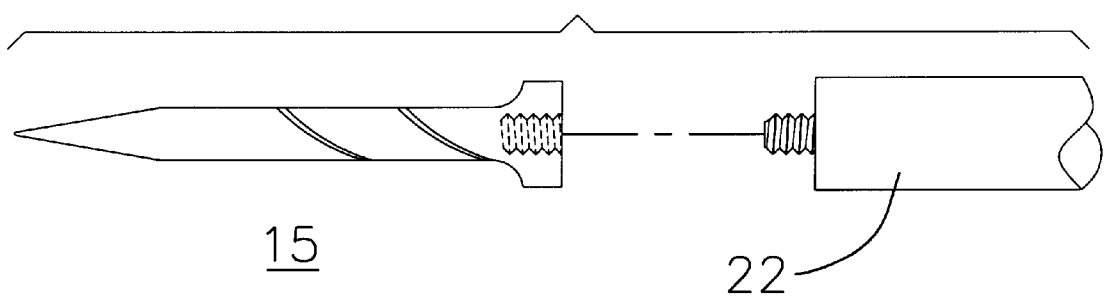

The preferred version is the operative tip 22 (as shown in FIGS. 3A–3B and FIGS. 4A–4B) having a female thread that accepts the male threads of a bit 15, and the operative tip 22 further having an outer sleeve 24 that is also threaded, so that the outer surface of the bit 15 can also be securely clamped. Here, the outer sleeve 24 is formed of a high strength material such as a stainless steel or a titanium alloy. The outer sleeve 24 of the operative tip 22 should have a female thread that securely locks onto the male threads of the outer surface of the bit 15. A various sample bits 15 are shown in FIGS. 5A–5C, and their use is shown in FIGS. 3A–3B and FIGS. 4A–4B. As shown therein, the bit 15 can perform a nailing operation or a drilling operation depending upon the formation of the operative tip 22. This preferred version allows the ultrasonic nailing and drilling apparatus 10 to be able to drill or nail into the material, and then retract the bit 15 (or a screw) upon the reversing of the motor 14. Having the outer sleeve 24 lockingly covering the outer surface of the bit 15 allows the bit 15 to be securely locked to the operative tip 22 during the reverse extracting of the bit 15 from the material drilled.

The ultrasonic nailing and drilling apparatus 10 further comprises of a shroud 26 that houses the piezoelectric transducer means 12. The piezoelectric transducer means 12 is generally a ceramic piezoelectric transducer, but other piezoelectric transducer can be used. Samples of a piezoelectric transducer assembly are well described in U.S. Pat. Nos. 4,169,984/4,838,853/4,867,715/4,828,052 and their patent specifications are incorporated herein.

However, other piezoelectric transducer means 12 are available, and the scope of the piezoelectric transducer means 12 should not be limited to the ones disclosed herein.

The piezoelectric transducer means 12 should have an axial bore 28, wherein the second horn end 20 of the elongated horn 16 extends through the axial bore 28 of the piezoelectric transducer means 12. The second horn end 20 of the elongated horn 16 extending through the axial bore 28 helps to transmit the vibration of the piezoelectric transducer means 12 to the elongated horn 16; thus to the operative tip 22. This version is preferred because the second horn end 20 of the elongated horn 16 becomes a part of the piezoelectric transducer means 12, and the ultrasonic vibration is better transmitted through the elongated horn 16.

The interface surface 30 between the elongated horn 16 and the piezoelectric transducer means 12 should be very finely grounded to eliminate any gaps, as the ultrasonic vibration can be reduced greatly if the interface surface 30 is not smoothly aligned. Moreover, the tightening of the piezoelectric transducer means 12 to the interface surface 30 should be between about 4,000 and 7,000 psi.

The ultrasonic nailing and drilling apparatus 10 further comprises of a housing 21, wherein the shroud 26 is rotatably attached within the housing 21. The piezoelectric transducer means 12 and the elongated horn 16 are fixedly attached within the shroud 26, but the elongated horn 16 and the operative tip 22 extend out of the shroud 26. The shroud 26 should be able to freely rotate within housing 21. For the best performance, the housing 21 should be a self lubricating bearing so the shroud 26 can rotate nearly frictionless within the housing 21, but other low friction bearings can be used. self lubricating bearings with the Frelon® bearing liner 32. Frelon® is known to be a mixture of Teflon® and fillers. A sample structure of a self lubricating bearing with Frelon® is an anodized aluminum outer body, with Frelon® inner layer bonded together by a bonding agent. Such a self lubricating bearings can be obtained from Pacific Bearings. The benefit of such Frelon® layered self lubricating bearings is numerous, and they include load transfer at molecular level, rust proof, self-aligning, maintenance free, and smooth and quiet operation.

For a better performance of the ultrasonic nailing and drilling apparatus 10, housing 21 can comprises of a horn cover 34 and a house bearing 36. The horn cover 34 has a first cover end 38 and a second cover end 40, wherein the horn cover 34 encloses a substantial portion of the elongated horn 16. The first cover end 38 is located toward the operative tip 22, and the second cover end 40 is fixedly attached to the house bearing 36. In this configuration, the house bearing 36 is the portion of the housing 21 that rotatably houses the shroud 26.

The motor 14 has a rotating arm 42. The motor 14 is fixedly attached to the housing 21, but the rotating arm 42 is fixedly attached to the shroud 26 so that the shroud 26 rotates as the rotating arm 42 rotates. Therefore, when the ultrasonic nailing and drilling apparatus 10 is switched on, the piezoelectric transducer means 12 is activated to give axial impulses on the elongated horn 16, and the rotating arm 42 of the motor 14 rotates the shroud 26 (and the piezoelectric transducer means 12 within the shroud 26) to give rotation to the elongated horn 16. Therefore, the piezoelectric transducer means 12 exerts axial impulses on the operative tip 22 and the rotating arm 42 of the motor 14 exerts a rotation on the operative tip 22 simultaneously.

For a better performance, as shown in FIG. 1, the rotating arm 42 should not directly attach to the piezoelectric transducer means 12. As shown, the rotation of the rotating arm 42 imparts a torque on the shroud 26, and the shroud 26 then imparts a torque on the elongated horn 16, but not directly to the piezoelectric transducer means 12.

Although various type of motors can be used, but for the best performance, the motor 14 should be a ultrasonic motor 44 that is able to rotate the rotating arm 42 bi-directionally; both clockwise and counter-clockwise, according to the need of the user. As the rotating arm 42 rotates bi-directionally, the ultrasonic nailing and drilling apparatus 10 can be used to screw in a screw into a very hard surface, and then to remove the screw out of a very hard surface. Moreover, the bit 15 can be drilled into the hard surface and the bit 15 can also be reversed out of the hard surface. The ultrasonic motor 44 is ideal for a delicate and precise operation, such as for medical or dental operations, as the ultrasonic motor 44 has high torque at lower rpm (revolutions per minute). Moreover, the ultrasonic motor 44 can easily controlled to vary its speed.

The ultrasonic nailing and drilling apparatus 10 according to this invention is highly efficient and effective, especially when the elongated horn 16 is fixedly attached to the shroud 26 and rotatably attached to the horn cover 34 at about two nodal points 46, 48 of the elongated horn 16. The nodal points 46, 48 are those points on the elongated horn 16 that has the least vibration, where the amplitude of the sinusoidal wave of the ultrasonic wave generated by the piezoelectric transducer means 12 is the lowest.

The nodal points 46, 48 of the ultrasonic wave created by the piezoelectric transducer means 12 are used to attach the elongated horn 16 and the shroud 26. Because when the nodal points 46, 48 are used, the vibration transmitted to the housing 21 is very minimal and the loss of the ultrasonic energy created by the piezoelectric transducer means 12 is minimized. Also, in order to minimize the loss of the ultrasonic energy, the point of contact at each of the nodal points 46, 48 should be also minimized. In order to achieve the minimization of the contact surface, rubber O-rings 50 can be used near the contact points. Although the rubber O-rings 50 do increase the overall surface area of the contact point, when the O-rings 50 are made of rubber, the energy loss is minimized. Moreover, to reduce the contact surface further, the point of contact can have one or more posts coming off the outer surface of the elongated horn 16 as the point of the attachment to the shroud 26.

The first nodal point 46 of the elongated horn 16 is located towards the piezoelectric transducer means 12, and the second nodal point 48 of the elongated horn 16 is located towards the operative tip 22. The first nodal point 46 of the elongated horn 16 can easily reach the inner wall of the shroud 26 if the elongated horn 16 has a broad portion about the first nodal point 46 of the elongated horn 16. The second nodal point 48 of the elongated horn 16 can be rotatably attached to the horn cover 34. The preferred version should have a cover bearing 51 fixedly attached to the horn cover 34, yet the second nodal point 48 of the elongated horn 16 is rotatably attached to the cover bearing 51. It is preferred to have both the house bearing 36 and the cover bearing 51 are self lubricating bearings.

Figure 2:
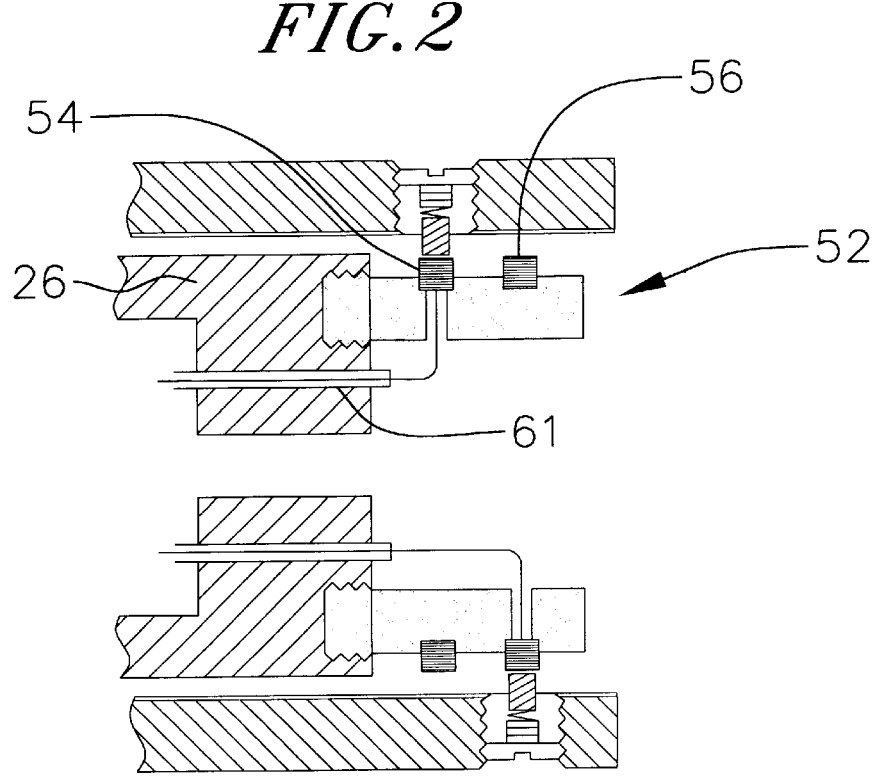
FIG. 2 is a cross-sectional view of a slip ring assembly used in this invention.
Figure 3A:
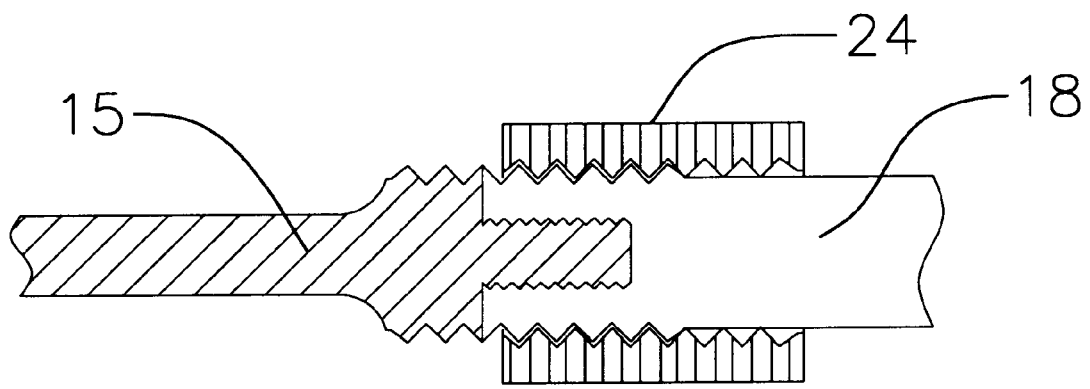
FIGS. 3A and 3B are respectively a cross-sectional view of an operative tip having an outer sleeve.
Figure 3B:
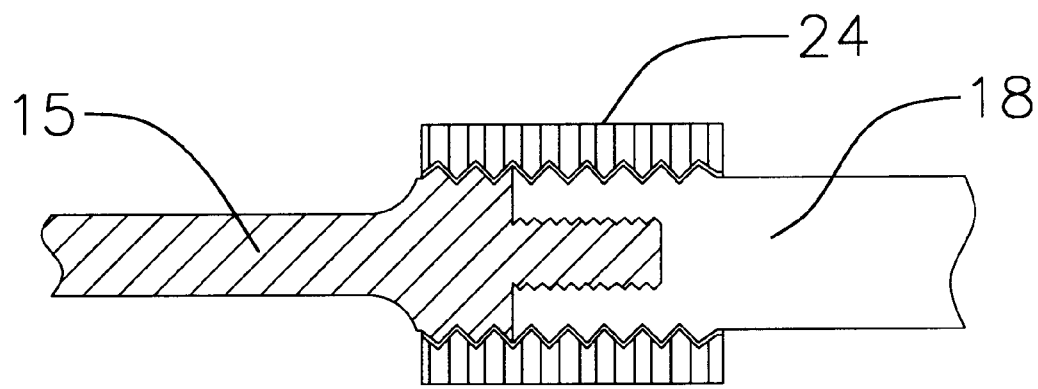
Figure 4A:
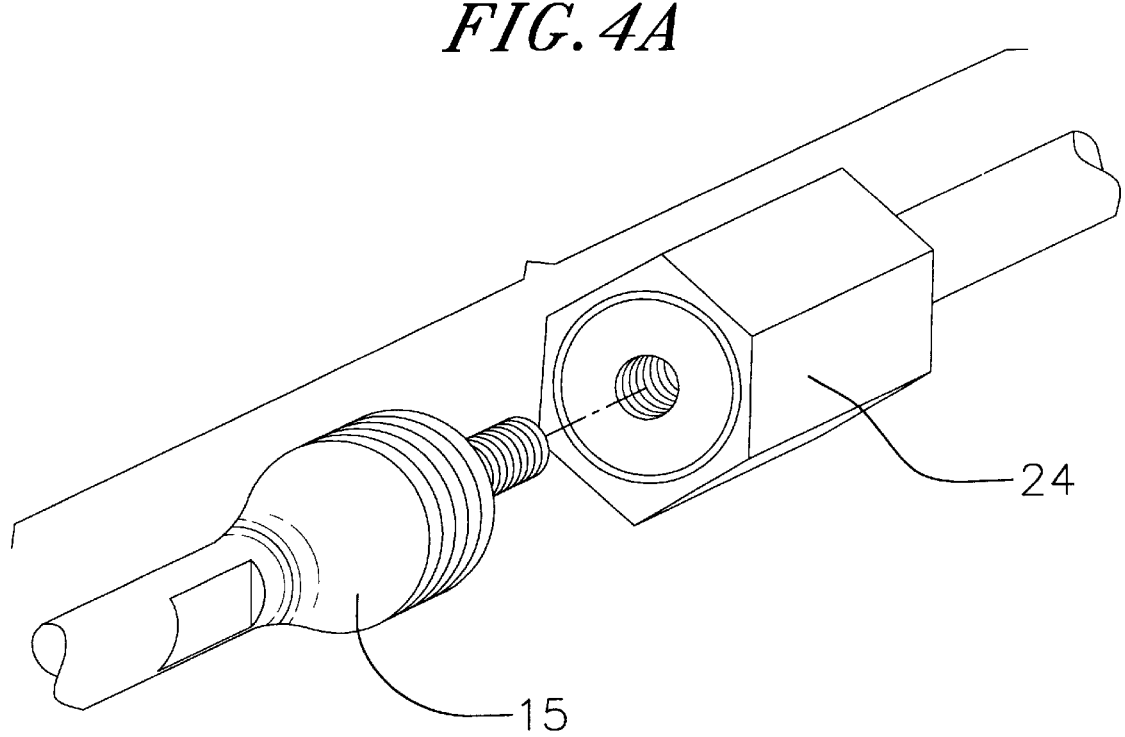
FIGS. 4A and 4B are respectively an exploded perspective view of the operative tip having an outer sleeve.
Figure 4B:
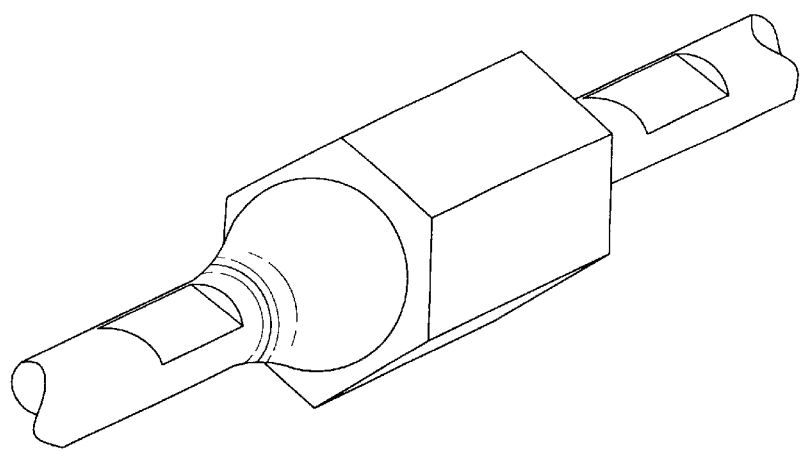

As shown in FIG. 2, because the shroud 26, along with the piezoelectric transducer means 12, needs to be rotating, a preferred version of the ultrasonic nailing and drilling apparatus 10 further comprises of a slip ring assembly 52 attached to the shroud 26 or the housing 21. The slip ring assembly 52 comprises of a first ring 54 and a second ring 56, wherein electrical power is supplied to the piezoelectric transducer means 12 thorough the first ring 54 and the second ring 56. The power to the slip ring assembly 52 is supplied through the housing 21, and the power to the piezoelectric transducer means 12 is supplied through a brush 58 or a cantilevered electrode 60 brushing over the first ring 54 and the second ring 56.

Each of the slip rings 54, 56 then carries the electrical current to the piezoelectric transducer means 12. Because the shroud 26 rotates, it is preferred that each electrical joint within the shroud 26 is securely attached, and perhaps covered with a light epoxy so that the soldering or other connecting means do not easily come apart.

To aid the torque from the rotating arm 42 of the motor 14 to efficiently transfer to the shroud 26, and to provide more secure hold of the elongated horn 16 and the piezoelectric transducer means 12 within the housing 21, the preferred version should have a rear plate 61 of the shroud 26 so that the rotating arm 42 of the motor 14 is securely fixed to the rear plate 61 of the shroud 26. The benefit of having the rear plate 61 is that more stability to the shroud 26 and the elongated horn 16 can be provided. Moreover, because another nodal point 62 is used to hold the shroud 26, the vibration transmitted to the housing 21 is very minimal.

The most preferred version further comprises of the housing 21 having a fluid inlet 64 and a fluid outlet 66, wherein a cooling fluid can be forced into the fluid inlet 64 and out of the fluid outlet 66 to cool the ultrasonic nailing and drilling apparatus 10. Because the elongated horn 16 can become very hot, cool air or even cold water can pass through the housing 21, through the horn cover 34. However, because a large amount of water over the elongated horn 16 reduces the effectiveness of the ultrasonic effect of the piezoelectric transducer means 12 transmitted through the elongated horn 16, cool or cold air is preferred.

The benefits of this inventions are numerous. First, the bit 15 can be drilled into the material and retracted out of the material. Second, the drilling using a ultrasonic device does not have to merely depend on the chipping action of the drill bit 15, but now actual rotation of the bit 15 is possible. Third, the speed of the rotation can be easily adjusted according to the material being nailed into or drilled into. Fourth, even for a simple nailing procedure, the slow rotation of the nail tip can enhance the penetrating effect of the nail. Fifth, because of the ultrasonic effect from the piezoelectric transducer, the torque on the rotating arm 42 does not need to be great. In fact, very little torque from the rotating arm 42 can improve the drilling procedure as the rotating bit 15 is also affecting the drilling surface ultrasonically.

Although the invention has been described in considerable detail with reference to certain preferred versions thereof, other versions are possible by converting the aforementioned construction. Therefore, the scope of the invention shall not be limited by the specification specified above and the appended claims.

What is claimed is:

1. An ultrasonic nailing and drilling apparatus comprising:

a) a housing having a horn cover and a house bearing, wherein the horn cover has a first cover end and a second cover end, wherein the horn cover encloses a substantial portion of the elongated horn, and wherein the second cover end is fixedly attached to the house bearing;

b) a piezoelectric transducer means having an axial bore;

c) an elongated horn having a first horn end, a second horn end, and a broad portion, wherein the first horn end forms an operative tip, wherein the second horn end extends through the axial bore of the piezoelectric transducer means and is attached to the transducer means, wherein the broad portion has a first nodal point of the elongated horn, wherein the elongated horn has a second nodal point of the elongated horn, and wherein the horn cover is rotatably attached to about the second nodal point of the elongated horn;

d) a shroud rotatably attached within the housing and fixedly attached to the elongated horn, wherein the shroud is fixedly attached to the elongated horn cat- about the first nodal point of the elongated horn, wherein the piezoelectric transducer means and the elongated horn are fixedly attached within the shroud, wherein the elongated horn and the operative tip extend out of the shroud, wherein the house bearing rotatably houses the shroud, and wherein the operative tip extends out of the housing; and e) a motor having a rotating arm, wherein the motor is a bi-directional ultrasonic motor, able to rotate clockwise and counter-clockwise and attached to the housing, wherein the rotating arm is fixedly attached to the shroud so that the shroud rotates as the rotating arm rotates, and wherein the shroud is rotatably attached within the housing, such that the piezoelectric transducer means exerts axial impulses on the operative tip and the rotating arm of the motor exerts a rotation on the operative tip simultaneously.

2. The ultrasonic nailing and drilling apparatus of claim 1 wherein the horn cover further comprises of a cover bearing, wherein the cover bearing is located near the first cover end, and the cover bearing is rotatably attached to about the second nodal point of the elongated horn.

3. The ultrasonic nailing and drilling apparatus of claim 2 wherein the housing further comprises of a slip ring assembly having a first ring and a second ring, wherein electrical power is supplied to the piezoelectric transducer means thorough the first ring and the second ring.

4. The ultrasonic nailing and drilling apparatus of claim 3 wherein the shroud further comprises of a rear plate wherein the rotating arm of the motor is fixedly attached to the rear plate of the shroud.

5. The ultrasonic nailing and drilling apparatus of claim 4 wherein the house bearing is a self lubricating bearing.

6. The ultrasonic nailing and drilling apparatus of claim 5 wherein the cover bearing is a self lubricating bearing.

7. An ultrasonic nailing and drilling apparatus comprising:

a) a housing having a fluid inlet, a fluid outlet, a horn cover and a house bearing, wherein a cooling fluid can be forced into the fluid inlet and out of the fluid outlet to cool the ultrasonic nailing and drilling apparatus, wherein the horn cover has a first cover end and a second cover end, wherein the horn cover encloses a substantial portion of the elongated horn, and wherein the second cover end is fixedly attached to the house bearing;

b) a piezoelectric transducer means having an axial bore, wherein the second horn end of the elongated horn extends through the axial bore of the piezoelectric transducer means;

c) an elongated horn having a first horn end, a second horn end, and a broad portion, wherein the broad portion of the elongated horn has a first nodal point of the elongated horn, wherein the elongated horn has a second nodal point of the elongated horn, wherein the horn cover is rotatably attached to about the second nodal point of the elongated horn, wherein the first horn end forms an operative tip, wherein the second horn end is attached to the transducer means;

d) a shroud rotatable attached within the housing, wherein the shroud is fixedly attached to the elongated horn at about the first nodal point of the elongated horn, wherein the piezoelectric transducer means and the elongated horn are fixedly attached within the shroud, and wherein the elongated horn and the operative tip extend out of the shroud, wherein the operative tip extends out of the housing, and wherein the house bearing rotatably houses the shroud;

e) a motor having a rotating arm, wherein the motor is a bi-directional ultrasonic motor, able to rotate clockwise and counter-clockwise and attached to the housing, wherein the rotating arm is fixedly attached to the shroud so that the shroud rotates as the rotating arm rotates, and wherein the shroud is rotatably attached within the housing, such that the piezoelectric transducer means exerts axial impulses on the operative tip and the rotating arm of the motor exerts a rotation on the operative tip simultaneously.

8. The ultrasonic nailing and drilling apparatus of claim 7 wherein the horn cover further comprises of a cover bearing, wherein the cover bearing is located near the first cover end, and the cover bearing is rotatably attached to about the second nodal point of the elongated horn.

9. The ultrasonic nailing and drilling apparatus of claim 8 wherein the housing further comprises of a slip ring assembly having a first ring and a second ring, wherein electrical power is supplied to the piezoelectric transducer means thorough the first ring and the second ring.

10. The ultrasonic nailing and drilling apparatus of claim 9 wherein the shroud further comprises of a rear plate wherein the rotating arm of the motor is fixedly attached to the rear plate of the shroud.

11. The ultrasonic nailing and drilling apparatus of claim 10 wherein the house bearing is a self lubricating bearing.

12. The ultrasonic nailing and drilling apparatus of claim 11 wherein the cover bearing is a self lubricating bearing.

* * * * *